(12) United States Patent
Boese et al.

(10) Patent No.: US 7,035,371 B2
(45) Date of Patent: Apr. 25, 2006

(54) METHOD AND DEVICE FOR MEDICAL IMAGING

(75) Inventors: Jan Boese, Eckental (DE); Reinmar Killmann, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/081,467

(22) Filed: Mar. 16, 2005

(65) Prior Publication Data

US 2005/0207529 A1  Sep. 22, 2005

(30) Foreign Application Priority Data

Mar. 22, 2004  (DE) .................... 10 2004 013 920

(51) Int. Cl.
*A61B 6/02* (2006.01)
(52) U.S. Cl. .......................................... 378/41; 378/62
(58) Field of Classification Search .................. 378/41, 378/62, 65, 98.12, 163, 205
See application file for complete search history.

(56) References Cited

U.S. PATENT DOCUMENTS

| | | | |
|---|---|---|---|
| 6,125,164 A * | 9/2000 | Murphy et al. ............... | 378/65 |
| 6,351,573 B1 | 2/2002 | Schneider | |
| 6,662,936 B1 | 12/2003 | Ikemoto et al. | |
| 6,865,253 B1 * | 3/2005 | Blumhofer et al. ........... | 378/65 |
| 2002/0049375 A1 | 4/2002 | Strommer et al. | |
| 2003/0181809 A1 | 9/2003 | Hall et al. | |

FOREIGN PATENT DOCUMENTS

| | | |
|---|---|---|
| DE | 196 20 371 A1 | 12/1997 |
| DE | 102 10 646 A1 | 10/2003 |
| DE | 102 10 647 A1 | 10/2003 |
| DE | 697 22 139 T2 | 2/2004 |
| EP | 0 843 870 B1 | 5/1998 |
| EP | 0 968 683 A1 | 1/2000 |
| EP | 1 124 201 A1 | 8/2001 |
| WO | WO 00/04830 | 2/2000 |
| WO | WO 02/052507 A1 | 7/2002 |
| WO | WO 03/083781 A1 | 10/2003 |

* cited by examiner

*Primary Examiner*—David V. Bruce
*Assistant Examiner*—Hoon Song

(57) ABSTRACT

The present invention relates to a method and a device for imaging during interventional or surgical procedures. In said method 2D fluoroscopy images (14a, 14b) of an area under examination are recorded by means of an X-ray fluoroscopy system and registered with previously recorded 3D image data (13) of the area under examination. The method is characterized in that two 2D fluoroscopy images (14a, 14b) are recorded in each case from a stereoscopic perspective as a 2D image pair, two 2D rendering images corresponding to the stereoscopic perspective of the 2D image pair are computed from the 3D image data (13), and the 2D image pair and the 2D rendering images are displayed stereoscopically as an overlay. The method and the device permit improved orientation for the operator in the area under examination.

11 Claims, 1 Drawing Sheet

METHOD AND DEVICE FOR MEDICAL IMAGING

CROSS REFERENCE TO RELATED APPLICATIONS

This application claims priority to the German application No. 10 2004 013 920.2, filed Mar. 22, 2004 which is incorporated by reference herein in its entirety.

FIELD OF INVENTION

The present invention relates to a method for imaging during interventional or surgical procedures, wherein 2D fluoroscopy images of an area under examination are recorded by means of an X-ray fluoroscopy system and registered with previously recorded 3D image data of the area under examination. The invention also relates to a device for performing the method.

BACKGROUND OF INVENTION

Interventional or surgical procedures are necessary in order to carry out numerous medical examinations. Such procedures are performed with the aid of X-ray systems. Thus, radiological interventions are frequently carried out for the purpose of diagnosing or treating vascular diseases, such interventions involving guiding an instrument, in particular a catheter, through a peripheral blood vessel to the point of interest in the body with the aid of X-ray fluoroscopy. Controlling an instrument of this kind can sometimes be very demanding, in particular if the blood vessels are very convoluted and have many branches. In order to improve navigation for the examining physician, an intervention of this kind is typically monitored by means of a monoplane or biplane imaging X-ray system. In this process the position of the instruments, such as, for example, catheters, guide wires or stents, can be captured very accurately in the X-ray images displayed during the intervention. However, in two-dimensional fluoroscopy images of this kind the three-dimensional anatomy of the patient can be recognized only to an inadequate degree. In certain interventional procedures, such as in neuroradiology, for example, and in electrophysiological examinations it is very difficult for the physician to find his or her bearings in the three-dimensional anatomy of the patient on the basis of the two-dimensional fluoroscopy images.

In order to improve orientation and therefore navigation it is known to record three-dimensional images of the area under examination prior to the intervention by means of a 3D imaging modality and display them during the intervention overlaid with the 2D fluoroscopy images. The three-dimensional images can be recorded prior to the examination using, for example, a magnetic resonance (MR), a computer tomography (CT), a positron emission tomography (PET) or a 3D ultrasound system. 3D angiography images can also be recorded in advance using the same angiography system by means of which the X-ray fluoroscopy images are also generated. The geometrical relationship between the image data sets must be known in any case for the subsequent 2D/3D overlaying of the images. This can be achieved either by calibration or by 2D/3D registration of the image data. Thus, for example, DE 102 10 646 A1 discloses a method of visualizing a medical instrument that has been introduced into an area of examination inside a patient, wherein the respective current position of the instrument in a three-dimensional environment is recognizable on a monitor by means of a 2D/3D registration and overlay of the aforementioned kind.

SUMMARY OF INVENTION

In the superimposed representation, however, the 3D data set is only presented to the viewer from the perspective of the current X-ray tube position. In this case the three-dimensional image information is furnished simply by means of special volume rendering methods (illumination models, shadow effects).

Starting from this prior art, an object of the present invention is to specify a method and a device for imaging during interventional or surgical procedures, by means of which the operator is provided with a better spatial orientation within the area under examination.

The object is achieved by the claims. Advantageous embodiments of the method and of the device are the subject matter of the dependent claims or can be derived from the following description and the exemplary embodiments.

With the present method for imaging during interventional or surgical procedures, 2D fluoroscopy images of an area under examination are recorded by means of an X-ray fluoroscopy system and registered with previously recorded 3D image data of the area under examination. The previously recorded 3D image data can be recorded for example by means of known 3D imaging techniques such as computer tomography, magnetic resonance tomography, positron emission tomography or a 3D ultrasound technique. When a monoplane or biplane X-ray system is used for the intervention that is to be performed, the 3D image data set can also be recorded by means of this device itself, for example in the form of 3D angiography images. The present method is characterized in that two 2D fluoroscopy images are recorded in each case from a stereoscopic perspective as a 2D image pair, two 2D rendering images corresponding to the stereoscopic perspective of the 2D image pair are computed from the 3D image data, and the 2D image pair and the 2D rendering images are displayed stereoscopically as an overlay.

The core of the present method is therefore the stereoscopic visualization of an overlay consisting of 3D image data and 2D X-ray fluoroscopy images of the area under examination. In this context a stereoscopic visualization is understood to mean a technique in which two images are presented separately from each other to the two eyes of the viewer from different viewing directions in order thereby to create a spatial impression. While generating two different views from the 3D image data set presents no particular difficulty, it is necessary to use two X-ray sources separated from each by a distance corresponding to the stereoscopic base for the X-ray recording of the two 2D fluoroscopy images in each case from a stereoscopic perspective or to switch the recording perspective accordingly.

The 2D fluoroscopy images of each 2D image pair are preferably recorded using two X-ray tubes separated from each other by a distance and a common detector. In this case the two 2D fluoroscopy images of each 2D image pair are recorded immediately after each other in time in order to avoid movement artifacts. In a further embodiment one X-ray tube having two X-ray focuses set at a distance from each other can also be used, the 2D fluoroscopy images of each 2D image pair being recorded by switching between said focuses.

Other techniques for generating the 2D fluoroscopy images from a stereoscopic perspective are, of course, also possible, for example through use of a deflection unit for the X-ray radiation, by means of which deflection unit it is possible to switch between two recording directions.

The device for performing the present method comprises an X-ray fluoroscopy system, in particular a monoplane or biplane X-ray system, for recording 2D fluoroscopy images of an area under examination from a stereoscopic perspective, a memory unit for storing 3D image data of the area under examination, a registration unit for registering recorded 2D fluoroscopy images with stored 3D image data and for computing the imaging geometry of the 2D fluoroscopy images, a rendering unit for computing two 2D rendering images from the 3D image data corresponding to the imaging geometry of the 2D fluoroscopy images, an overlay unit for weighted overlaying of the 2D rendering images with the respective associated 2D fluoroscopy images, and a stereoscopic display unit for the stereoscopic visualization of the overlaid images. In this context the term "rendering" is understood to mean the computation of a two-dimensional representation of a three-dimensional image data set.

By means of the present method and the associated device the viewer is presented with the 3D image data set from two different, stereoscopic viewing directions. In this way, in combination with the stereo display, a spatial impression of the three-dimensional data set is conjured up in the viewer. Since the 2D fluoroscopy images are also recorded from these two viewing directions, the instruments that are recognizable in these images can be represented spatially and in this way can also be located vertically to the detector plane for the viewer. The superimposed stereoscopic visualization provides the physician with an optimal means of orientation in the area under examination during the intervention.

The stereoscopic visualization of the overlaid images can be realized in different ways. Stereoscopic display techniques are known from the computer vision field. Thus, for example, shutter glasses can be used to enable the viewer to perceive the stereoscopic effect in conjunction with a corresponding clock-timed image display on a monitor. Furthermore stereo monitors, for example, are also known which have suitable lens arrays for producing the stereoscopic effect even without additional glasses. Said lens arrays cause each of the viewer's eyes to perceive a different image on the monitor.

BRIEF DESCRIPTION OF THE DRAWINGS

The present method and the associated device will be explained again in more detail below with reference to an exemplary embodiment in connection with the drawings, in which.

DETAILED DESCRIPTION OF INVENTION

Figure 1:
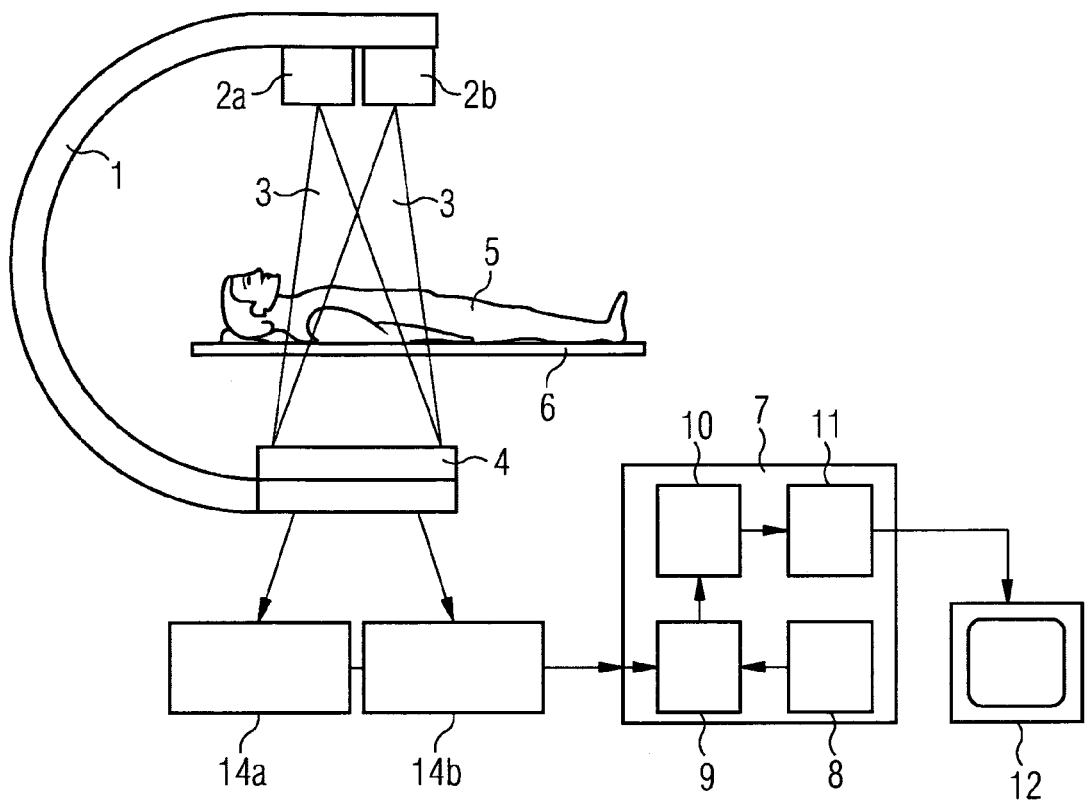
FIG. 1 shows an example of a C-arm device for performing the present method.

FIG. 1 shows by way of example an X-ray recording system according to the present invention which is embodied as a monoplane C-arm device. Mounted on the C-arm 1 of this X-ray recording system are two separate X-ray tubes 2a, 2b which direct the X-ray radiation 3 onto a common detector 4 which is mounted on the opposite side of the C-arm 1. A stereoscopic base is established by the distance separating the two X-ray tubes 2a, 2b, thereby enabling the subsequent stereoscopic viewing of the images. Owing to the recording geometry provided, the area under examination of a patient 5 lying on a movable table 6 can be captured or recorded from two different perspectives virtually simultaneously. The recording geometry, in particular the position of the two X-ray tubes 2a, 2b and the detector 4, a multi-row detector array, is recorded in a memory 8 of the image analysis device 7. Also stored in this memory 8 is 3D image data 13 that was recorded prior to the intervention by means of a 3D imaging modality such as, for example, MR, CT or 3D angiography.

Figure 2:
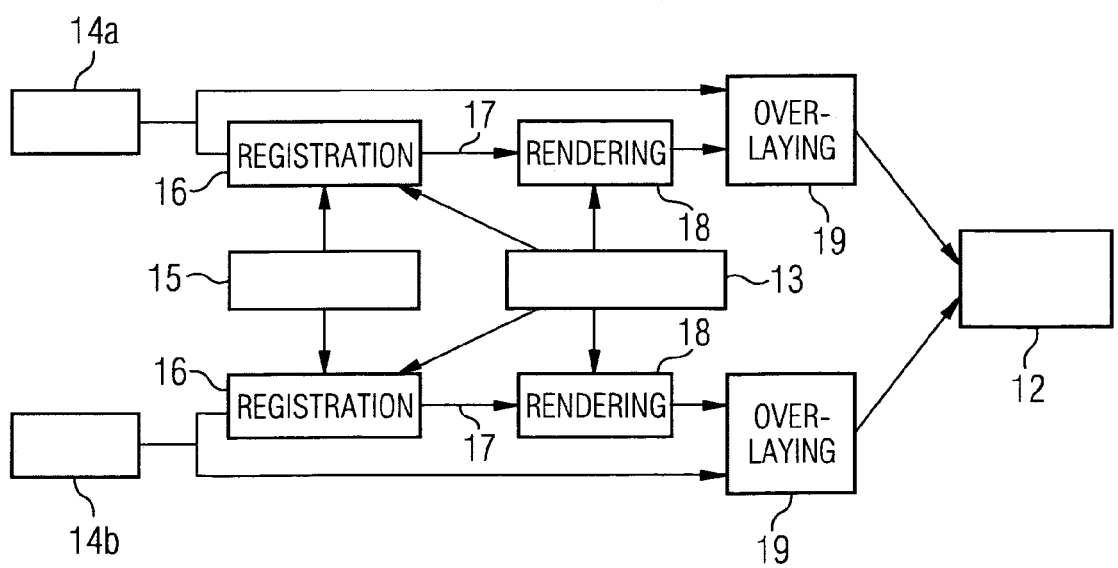
FIG. 2 shows an example of the individual steps in the performance of the present method.

In the performance of the present method, as also represented in overview form in FIG. 2, the two 2D fluoroscopy images 14a and 14b are generated by alternate switching of the X-ray tubes 2a and 2b, said fluoroscopy images 14a and 14b corresponding to the different viewing directions defined by the position of the two X-ray tubes 2a, 2b. These two defined viewing directions are referred to in the present patent application as the stereoscopic perspective.

The two fluoroscopy images 14a, 14b are registered by means of the 2D/3D registration unit 9 with the aid of the recording geometry 15 stored in the memory 8 with the 3D data set 13 likewise stored in the memory 8. This 2D/3D registration 16 results in the imaging geometry 17 of the 2D fluoroscopy images 14a, 14b.

The purpose of the 2D/3D registration is to determine the geometrical relationship between 3D data set and the projection geometry of the two 2D fluoroscopy images. In addition to the use of the known recording geometry 15 of the fluoroscopy images, the 2D/3D registration can also be performed on the basis of the information from the image data of the 2D image 14a/14b and the 3D image data 13 or from a possibly known recording geometry of the 3D image data 13 if the latter was recorded by means of the same X-ray recording system, such as, for example, in the case of 3D angiography. A combination of the aforementioned information is also possible for the 2D/3D registration.

With the aid of the imaging geometry 17 two two-dimensional images are computed in the rendering unit 10 from the 3 D data set 13, which images correspond to the viewing directions of the respective X-ray tubes 2a, 2b or, as the case may be, the imaging geometry 17 of the two 2D fluoroscopy images 14a, 14b. Finally, the two 2D rendering images computed by means of rendering 18 are overlaid in the overlay unit 11 with the two 2D fluoroscopy images 14a, 14b. The overlaying 19 is of course performed separately for each viewing direction or perspective. During this overlaying 19 the two, in each case two-dimensional, images, i.e. one 2D fluoroscopy image in each case and one 2D rendering image in each case, are merged with each other. The resulting output image or output image pair is a weighted sum of the input images, whereby the weights can be selected arbitrarily according to the desired type of visualization.

The two output images are then displayed via a stereo display 12. Said stereoscopic display 12 ensures that the two output images corresponding to different viewing angles are shown to each of the viewer's eyes separately. The viewer thus perceives the displayed images as a spatial image which greatly facilitates his or her orientation within the area under examination.

The invention claimed is:

1. A method of acquiring medical images of an examination area during a medical procedure applied to a patient, comprising:

recording three-dimensional image data of the examination area;

recording a plurality of two-dimensional images of the examination area during the medical procedure using an X-ray imaging device; and registering the two-dimensional images with the three-dimensional image data, wherein the two-dimensional images include a plurality of image pairs each corresponding to a stereoscopic perspective, for each image pair, a further pair of two-dimensional rendering images corresponding to the image pair is processed using the three-dimensional image data, and displaying a superimposed image including the image pair and the corresponding two-dimensional images, the superimposed image having a stereoscopic perspective.

2. The method according to claim 1, wherein the medical procedure includes treating an examination area of the patient with a medical instrument.

3. The method according to claim 2, wherein the medical procedure is a surgery.

4. The method according to claim 2, wherein the medical instrument is a scalpel or a catheter.

5. The method according to claim 1, wherein the image pairs are recorded by two separate X-ray tubes having a common detector.

6. The method according to claim 1, wherein the superimposed image is displayed on a stereoscopic monitor.

7. The method according to claim 1, wherein registering the two-dimensional images with the three-dimensional image data is based on a known imaging geometry related to the two-dimensional images.

8. The method according to claim 1, wherein the three-dimensional-image data and the two-dimensional images are recorded using the same x-ray imaging device, and registering the two-dimensional images with the three-dimensional image data is based on a known imaging geometry of the three-dimensional image data.

9. The method according to claim 1, wherein registering the two-dimensional images with the three-dimensional image data is based on image information extracted from the two-dimensional images and the three-dimensional image data.

10. A device for acquiring medical images of an examination area during a medical procedure applied to a patient, comprising:

an X-ray imaging device for recording a plurality of two-dimensional images of the examination area from, the two-dimensional images including a stereoscopic perspective of the examination area;

a memory unit for storing three-dimensional image data of the examination area;

a registration unit for registering the two-dimensional images with the three-dimensional image data and for calculating an imaging geometry related to the two-dimensional images;

a rendering unit adapted to generate two two-dimensional rendering images using the three-dimensional image data, the two two-dimensional rendering images corresponding to the imaging geometry;

a superimposing unit for generating a superimposed image created by overlaying of the two-dimensional rendering images with the corresponding two-dimensional images; and a stereoscopic display unit for displaying the superimposed image, the superimposed image having a stereoscopic perspective, wherein overlaying of the two-dimensional rendering images with the corresponding two-dimensional images includes weighting image information of either the two-dimensional rendering images or the two-dimensional images.

11. The device according to claim 10, wherein the stereoscopic display unit is a stereoscopic monitor.

* * * * *